United States Patent [19]
Harnoncourt et al.

[11] Patent Number: 5,266,180
[45] Date of Patent: Nov. 30, 1993

[54] INTERIOR ELECTRODE OF A POLAROGRAPHIC ELECTRODE

[75] Inventors: Karl Harnoncourt, Graz; Erich Kleinhappl, Weinitzen; Dieter Pätzold, Graz, all of Austria

[73] Assignee: AVL Medical Instruments AG, Schaffhausen, Switzerland

[21] Appl. No.: 894,549

[22] Filed: Jun. 5, 1992

[30] Foreign Application Priority Data

Jun. 27, 1991 [AT] Austria ................................. 1291/91

[51] Int. Cl.$^5$ ............................................. G01N 27/31
[52] U.S. Cl. .................... 204/415; 204/153.17; 422/82.01
[58] Field of Search ................... 204/415, 153.17; 422/82.01–82.04, 98

[56] References Cited

U.S. PATENT DOCUMENTS

| | | | |
|---|---|---|---|
| 3,700,580 | 10/1977 | MacLeod et al. | 204/415 |
| 3,999,284 | 12/1976 | Bicher | 204/415 X |

FOREIGN PATENT DOCUMENTS

| | | | |
|---|---|---|---|
| 359750 | 11/1980 | Austria . | |
| 2059073 | 4/1981 | United Kingdom | 204/415 |
| 2114304 | 8/1983 | United Kingdom . | |

Primary Examiner—Jill A. Johnston
Attorney, Agent, or Firm—Watson, Cole, Grindle & Watson

[57] ABSTRACT

In order to simplify manufacture of the interior electrode of a polarographic electrode with an electrically insulating shell containing a wire lead and carrying a reactive surface at its front end, which surface is formed by the free cross-sectional areas of wires arranged in the shell and in electrical contact with the wire lead, the wires and the site where they are connected to the wire lead are embedded in a plastic compound filling the front end of the shell.

7 Claims, 3 Drawing Sheets

INTERIOR ELECTRODE OF A POLAROGRAPHIC ELECTRODE

BACKGROUND OF THE INVENTION

This invention relates to an interior electrode of a polarographic electrode with an electrically insulating shell containing a wire lead and carrying a reactive surface at its front end, which surface is formed by the free cross-sectional areas of wires arranged in the shell the wires being in electrical contact with the wire lead, and to a method of manufacturing such an interior electrode.

To facilitate measuring, the wires of such an interior electrode are extremely thin, with diameters of about 0.01 mm, and comparatively long. They must be smooth and, above all, free of bends and breaks when they are sealed into the electrode, and they must be in good electrical contact with the wire lead. Because of these requirements and the thinness of the wires, such electrodes are difficult to produce.

DESCRIPTION OF THE PRIOR ART

An interior electrode of the above type is disclosed in AT-PS 359 750, which is made in the following way. First of all, the wire lead and a round glass rod are firmly attached to each other, forming a semispherical transition from the thinner wire to the thicker glass rod. At the transition region forming a supporting area the thin wires are connected with the wire lead so as to be electrically conductive, and are bent over the semispherical supporting area and bonded to the glass rod by means of an adhesive compound. Then the assembly consisting of wire lead and glass rod with attached wires is placed into a glass shell, whose inner diameter corresponds to that of the glass rod with the affixed electrode wires. The end of the glass pipe is sealed together with the glass rod, such that the thin electrode wires are completely sheathed by the glass. In this context it is important that the dimensions of the individual components be perfectly matched in order to compensate for the expansion and shrinkage occurring during processing and to prevent them from doing damage to the thin wires. Finally, the electrode tip is inspected with the microscope for the area where the sealed-in wires are distributed most uniformly, and the electrode is cut off at this place. The disadvantage of this type of interior electrode is the extremely complex manufacturing process with its high percentage of rejects and high cost arising therefrom.

U.S. Pat. No. 3,700,580 shows an electrochemical sensor in which the interior electrode is configured as a wire which is connected to a wire lead, wire and connecting site being potted in epoxide resin. A similar variant is known from GB-PS 2,114,304.

SUMMARY OF THE INVENTION

It is an object of the invention to propose an interior electrode of the above type, which may be manufactured in a simpler manner without impairing measuring sensitivity.

This object is achieved in the invention by conventionally embedding the wires and the site where they are connected with the wire lead in a plastic compound filling the front end of the shell, and by providing that the shell, relative to the inner diameter at the front end, have a reduced cross-section between the connecting site and the reactive surface, where the wires touch the walls of the shell and are directed essentially parallel to the axis of the shell.

In the invention a method of manufacturing such an interior electrode is characterised in that the wire lead including the wire ends sticking out therefrom is pulled into the shell by the free end of the wire lead, such that the wire ends touch the walls of the shell in the region of reduced cross-section and are thus given a direction essentially parallel to the axis of the shell, and further that the front end of the shell is filled in a known manner with a plastic compound, and that its surface is finished (e.g., by grinding) after the plastic compound has cured, in order to expose the cross-sectional areas of the wire ends. This will ensure in a simple manner that the thin electrode wires are embedded in the potting compound practically without any voids, and that they are not caught in the transitional region between shell material and plastic compound.

Basically, the above casting method is suited for the manufacture of all electrodes operating according to the amperometric principle, including, among others, electrodes for measuring $O_2$, glucose, lactate, etc.

The electrode of the invention is particularly advantageous in applications where the substance to be determined (for instance, oxygen) is consumed and only small sample volumes are available.

An advantageous connection between the wire lead and the wires ending in the reactive surface is obtained by providing that two wires form the free ends of a piece of wire and the wire lead have a flat portion at the site where it connects to the piece of wire, which flat portion embraces the piece of wire in hook-wise fashion. Of course, the wire lead and the thin wires could also be joined by soldering or with the use of an adhesive.

A further advantage is gained by providing the shell of the interior electrode with a step upon which the flat portion of the wire lead rests. When the thin wires are inserted into the shell, the wire lead may be threaded until a stop is reached, without having to be adjusted accurately.

In the invention the electrode shell may be made of glass, ceramics or a plastic material, and the plastic compound may consist of epoxide resin (as is known in the art), polyester or liquid polymethyl methacrylate, and the wires of precious metal, precious metal alloy or carbon fibers. Suitable shell-building materials thus do not only include glass and ceramics, but the insulating shell may also be configured as a plastic component made by mechanical processes or injection-moulding, all materials with satisfactory bonding to the potting compound being acceptable. Preferred wire materials are gold, platinum, silver, iridium and carbon fibers; using a plastic potting material will also permit the use of wire materials that cannot be sealed into glass.

Desirable properties of the potting material are low shrinkage upon curing, good adhesion to both wires and shell material, good insulation, low water absorption, low gas permeability and good machinability. Another advantage of an interior electrode as specified by the invention is its low manufacturing cost.

BRIEF DESCRIPTION OF THE DRAWINGS

Following is a more detailed description of the invention as illustrated by the attached drawings, in which.

DETAILED DESCRIPTION OF THE PREFERRED EMBODIMENT

Figure 1:
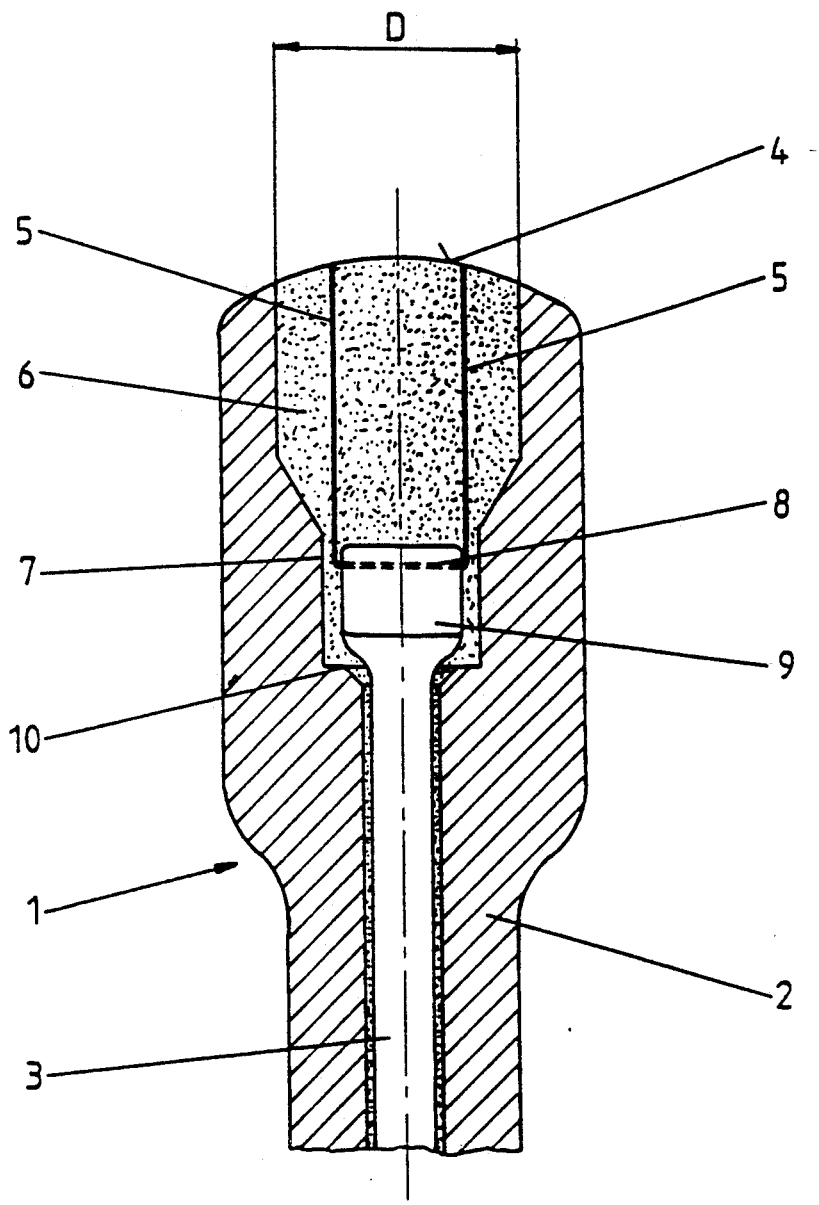
FIG. 1 shows a sectional view of an interior electrode of a polarographic electrode, as specified by the invention.

The interior electrode 1 presented in FIG. 1 has an electrically insulating shell 2 containing a wire lead 3. The reactive surface 4 of electrode 1 is formed by the free cross-sectional areas of the wires 5, which are in electrical contact with the wire lead 3. The wires 5 and the site where they are connected to the wire lead 3 are embedded in a plastic compound filling the front end of the shell 2.

The inner diameter D of shell 2 has a reduced cross-section 7, where the wires 5 touch the walls of the shell upon insertion of the wire lead 3 and are directed towards the reactive surface 4.

Figure 3:
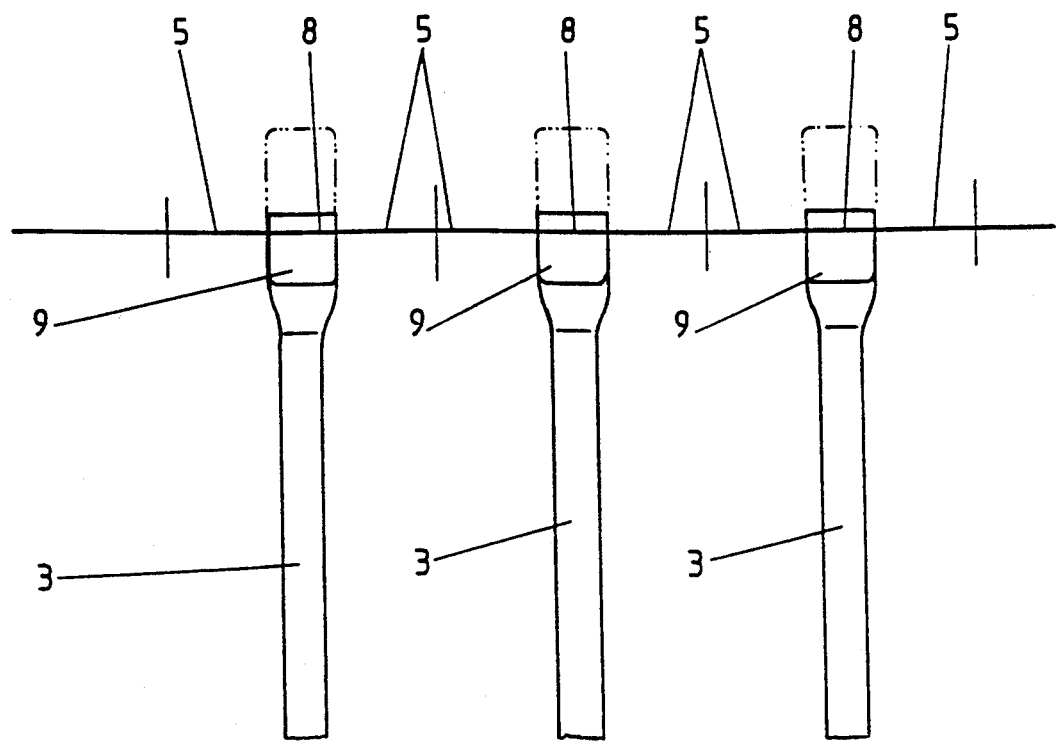
Figure 4:
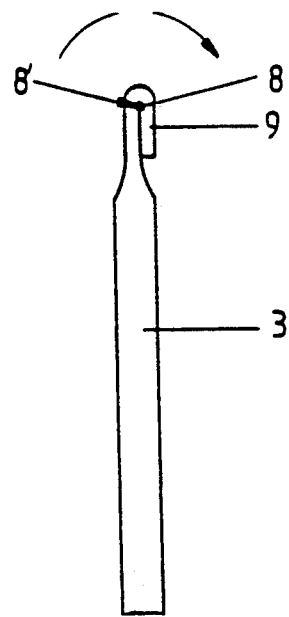

Connecting the wires as shown in FIG. 1 and, using details, in FIGS. 3 and 4, is performed in several steps. At first a number wire leads 3 of conventional wire, e.g. made of copper, i.e., polished, zinc-plated or silver-plated, or of silver, with a diameter of 0.5 mm approx., are cut and cold-formed on one end, producing flat portions 9 of a width of 1 mm approx. The wire leads 3 with their flat portions 9 are placed side by side, leaving given spaces to allow a thin wire, for instance made of platinum, with a diameter of 5 to 50 micrometers, to be placed across the flat portions 9 (FIG. 3). The the flat portions 9 are bent over in hook-wise fashion, such that the platinum wire is embraced and held. The platinum wire is cut between each pair of wire leads, such that each wire lead 3 grips a piece of wire 8, whose free ends sticking out at a right angle constitute the wires 5. Electrical conductivity of the connecting site between wire lead 3 and wire piece 8 may be increased with a drop of conductive adhesive (arrow 8') in FIG. 4.

Then the wire lead 3 is pulled into the shell 2 by its free end, until its flat portion 9 rests against a step 10 of the shell 2, the wire ends or wires 5 being directed towards the reactive surface 4 by the reduced cross-section 7. The front end of the shell 2 is now filled with a plastic compound 6. After the curing process, protruding parts of the compound are removed mechanically, for instance by grinding, and the surface is polished.

Figure 2:
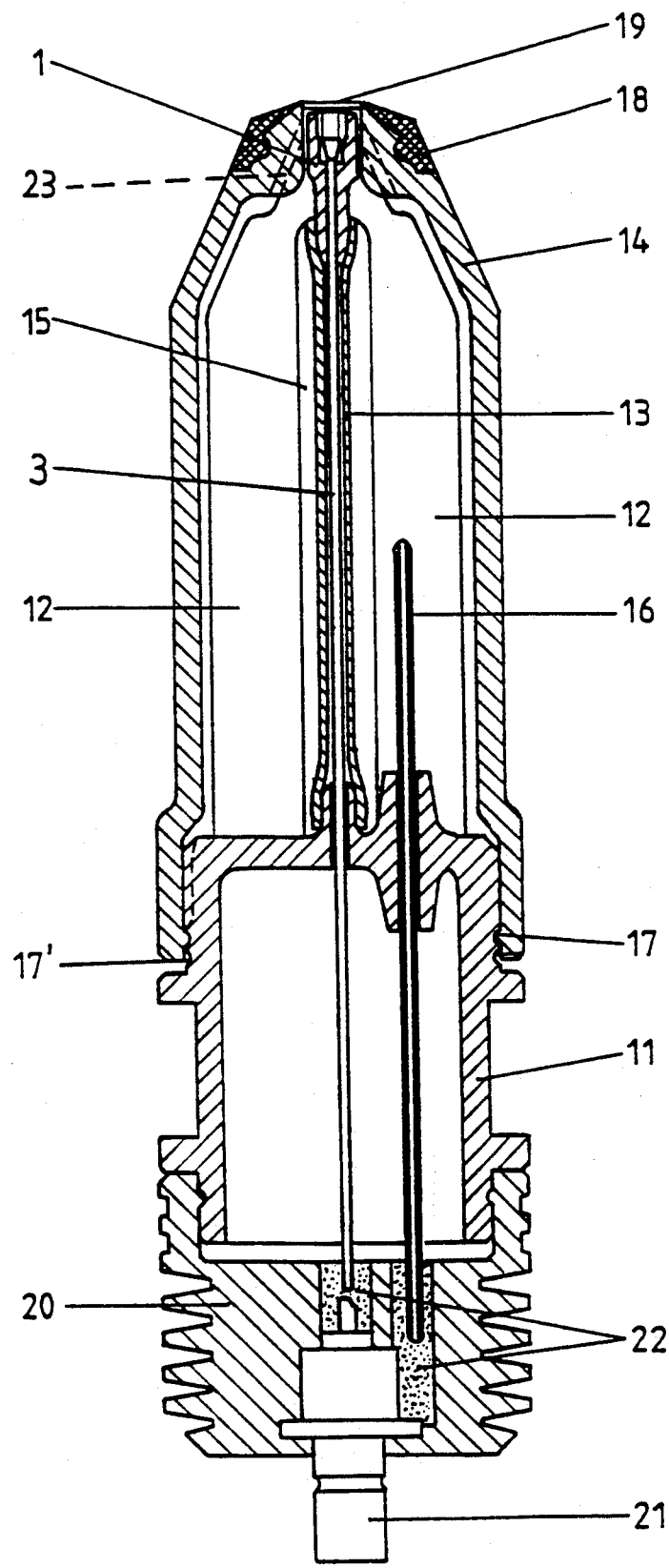
FIG. 2 shows a polarographic electrode with an interior electrode as in FIG. 1, FIGS. 3 and 4 give details from the manufacturing process.

FIG. 2 shows a polarographic electrode with the interior electrode 1 inserted, which latter is held by ribs 12 formed integral with the electrode body 11. Between the electrode body 11 and the interior electrode 1 the wire lead 3 is surrounded by a flexible sleeve 13 and is electrically insulated. The interior 15 of the polarographic electrode, which is formed by a housing 14 and filled with an electrolyte, has a reference electrode 16 projecting into it, which is configured as a silver pin held by the electrode body 11. Expansions, for instance of the air in the electrolyte chamber, which are due to temperature and design, are compensated by the flexible sleeve 13.

The housing 14 locks onto the electrode body via two locking positions, and is provided with a soft cap 18 at the entrance point of the interior electrode 1, a membrane 19 selective to the test substance forming part of the cap. The ribs 12 formed integral with the electrode body 11 lock with recesses 23 of the housing 14, preventing the latter from turning and thus relieving the membrane 19 from any additional load. The cap 18 serves as a membrane support in addition to sealing off a measuring chamber.

When the electrode is inserted into a measuring chamber V, the housing 14 is pushed into the second locking position 17', thus stretching the membrane 19 and pulling it against the interior electrode 1; in this way the working life of the electrode is determined by its actual use in the measuring chamber, and, as a consequence, considerably extended. The slight overpressure caused by inserting the electrode again is compensated by the flexible sleeve 13.

At the end facing away from the interior electrode 1, the polarographic electrode has a plug base 20 with an integrated plug pin 21, electrical contact with the wire lead 3 on the one hand and with the reference electrode 16 on the other hand being established via connections using a conductive adhesive 22.

We claim:

1. An interior electrode of a polarographic electrode which comprises an electrically insulating sheel having outer walls, inner walls, a front end and containing a plurality of wire means arranged in said shell, said wire means having free cross-sectional areas forming a reactive surface at said front end of said shell, and having an electrical connection with a wire lead inside said shell, wherein said wire means and said electrical connection with said wire lead are embedded in a plastic compound filling said front end of said shell, and wherein said shell, relative to an inner diameter at said front end, has a first reduced cross-section in proximity of said electrical connection where said wire means touch said inner walls of said shell and are directed essentially parallel to an axis of said shell.

2. An electrode according to claim 1, wherein two of said plurality of wire means are provided by opposite end portions of a single piece of wire, and said wire lead has a flat portion which embraces a middle portion of said single piece of wire in a hook-wise fashion, forming said electrical connection.

3. An electrode according to claim 2, wherein said shell defines a second reduced cross section that provides a step upon which said flat portion of said wire lead rests.

4. An electrode according to claim 1, wherein said electrically insulating shell is made of at least one of the following materials: ceramics and plastic material.

5. An electrode according to claim 1, wherein said plastic compound consists of at least one of the following materials: epoxide resin, polyester and liquid polymethyl methacrylate.

6. An electrode according to claim 1, wherein said wires arranged in said shell consist of at least one of the following materials: precious metal, precious metal alloy and carbon fibers.

7. An interior electrode for a polarographic electrode which comprises:

an elongated, electrically insulating shell which provides a front end, a rear end, and an axis along a length thereof, said shell also defining an interior channel that extends from said front end towards said rear end, said channel having a first cross sectional area at said front end and a second cross sectional area at a predetermined position between said front end and said rear end, said second cross sectional area being smaller than said first cross sectional area, a wire lead positioned in said channel that extends from said predetermined position towards said rear end of said shell, a plurality of wire means electrically connected to said wire lead which extend from said wire lead to free ends that are exposed at said front end of said shell, said wire means extending in parallel with said axis, said free ends forming a reactive surface at said front end of said shell, and said wire means contacting said shell adjacent said predetermined position, and a plastic compound filling said channel between said wire means and between said wire means and said shell.

* * * * *